United States Patent
Peterson et al.

(10) Patent No.: US 6,214,889 B1
(45) Date of Patent: *Apr. 10, 2001

(54) TOPICAL APPLICATION OF FORMATE FOR RELIEF OF ADVERSE SKIN CONDITION FOR HUMANS

(76) Inventors: Thomas E. Peterson, 1143 Rennie, Katy, TX (US) 77450; Byron A. Church, 1814 Rosewood La., Sugar Land, TX (US) 77479

( * ) Notice: Subject to any disclaimer, the term of this patent is extended or adjusted under 35 U.S.C. 154(b) by 0 days.

This patent is subject to a terminal disclaimer.

(21) Appl. No.: 08/971,413

(22) Filed: Nov. 17, 1997

(51) Int. Cl.[7] .............. A61P 17/06; A61P 17/08; A61P 17/00
(52) U.S. Cl. .............. 514/830; 514/861; 514/863; 514/864
(58) Field of Search .................... 424/401, 400, 424/484; 514/887, 861, 865, 830, 557, 944

(56) References Cited

U.S. PATENT DOCUMENTS 4,196,218 * 4/1980 Thiele .................. 424/318
5,874,474 * 2/1999 Peterson et al. ............ 514/578

* cited by examiner

*Primary Examiner*—Edward J. Webman
(74) *Attorney, Agent, or Firm*—Akin, Gump, Strauss, Hauer & Feld, L.L.P.

(57) ABSTRACT

The topical application of formate to treat common skin ailments such as acne, alopecia, psoriasis, eczema, seborrhea, dermatitis, chronic itching, tinea infections, and insect bites.

5 Claims, No Drawings

TOPICAL APPLICATION OF FORMATE FOR RELIEF OF ADVERSE SKIN CONDITION FOR HUMANS

FIELD OF THE INVENTION

This invention relates to a topical application for humans and a method of preparing the same, used to treat adverse skin conditions.

Topical applications for humans for the relief of adverse skin conditions are aqueous based lotions, sprays or ointments applied directly to the human skin. The applications perform several functions such as drying the skin and inhibiting infection.

It is an object of this invention to provide an improved topical application for humans for the relief of common skin ailments particularly those caused by, but not limited to acne, alopecia, psoriasis, eczema, seborrhea, dermatitis, chronic itching, numerous varieties of tinea, and insect bites.

In accordance with this invention, a topical application for humans consists of purified or distilled water combined with potassium, and/or sodium, and/or calcium, and/or cesium formate in any concentration from 0.1% to 99.1% for each product in liquid form or together with a gelling agent to form a gel application. Preferably, the potassium, and/or sodium, and/or cesium formate is present in a concentration of about 50% by volume, or within the range of about 40–60% by volume, in a liquid form with a gelling agent to form a gel application. One of the advantages of this invention is that it brings about rapid relief and recovery by drying the epidermis and speeding the healing process.

One of the peculiarities of the invention lies in the active ingredient which promotes healing. Many medications currently on the market rely on steroids, antibiotics or vitamin A cream for relief of the skin problem. This invention relies on potassium, and/or sodium, and/or calcium, and/or cesium formate to promote healing.

Topical applications are administered directly on the affected area. The duration of treatment depends upon the severity of the dermatitis. Several applications may be necessary for complete healing.

Although this invention has been disclosed and described in its preferred forms with a certain degree of particularity, it is understood that the present disclosure of the preferred forms is only by way of example and numerous changes in the details of operation and in the combination and arrangement of parts may be resorted to without departing from the spirit and scope of the invention as hereinafter claimed.

What is claimed is:

1. A method of treating human skin ailments, the method comprising applying a liquid or gel composition to the epidermis of a human, the liquid or gel composition comprising one or more of potassium formate, sodium formate, calcium formate and cesium formate.

2. The method of claim 1 wherein the liquid or gel composition further comprises purified or distilled water in which one or more of the potassium formate, sodium formate, calcium formate and cesium formate is present in a concentration from 0.1% to 99.1% by volume.

3. The method of claim 1 wherein the liquid or gel composition further comprises purified or distilled water in which one or more of the potassium formate, sodium formate, calcium formate and cesium formate is present in a concentration from 40% to 60% by volume.

4. The method of claim 1 wherein the liquid or gel composition further comprises purified or distilled water in which one or more of the potassium formate, sodium formate, calcium formate and cesium formate is present in a concentration of about 50% by volume.

5. A method of treating human skin ailments caused by psoriasis, eczema, seborrhea, dermatitis, chronic itching and insect bites, the method comprising applying a liquid or gel composition to the epidermis of a human, the liquid or gel composition comprising one or more of potassium formate, sodium formate, calcium formate and cesium formate.

* * * * *